United States Patent [19]
Hill et al.

[11] Patent Number: 4,731,330
[45] Date of Patent: Mar. 15, 1988

[54] WHOLE BLOOD CONTROL SAMPLE

[75] Inventors: James L. Hill, San Jose; Laura J. Winfrey, Belmont, both of Calif.

[73] Assignee: Biotrack, Inc., Mt. View, Calif.

[21] Appl. No.: 880,696

[22] Filed: Jul. 1, 1986

[51] Int. Cl.$^4$ .................. G01N 31/00; G01N 33/86
[52] U.S. Cl. ........................................ 436/16; 436/69; 436/10; 436/18
[58] Field of Search ...................... 436/8–18, 436/69, 176; 435/2; 424/3, 11; 422/61

[56] References Cited

U.S. PATENT DOCUMENTS

| | | | |
|---|---|---|---|
| 3,714,345 | 1/1973 | Hirata | 436/10 |
| 3,715,427 | 2/1973 | Hirata | 436/10 |
| 4,157,383 | 6/1979 | Sedlacek et al. | 436/10 |
| 4,219,440 | 8/1980 | Runck et al. | 436/16 |
| 4,324,686 | 4/1982 | Mundschenk | 436/10 |
| 4,324,687 | 4/1982 | Louderback et al. | 436/10 |
| 4,412,004 | 10/1983 | Ornstein et al. | 436/16 |
| 4,438,002 | 3/1984 | Engler et al. | 436/16 |
| 4,572,899 | 2/1986 | Walker et al. | 436/16 |

*Primary Examiner*—Barry S. Richman
*Assistant Examiner*—T. J. Wallen
*Attorney, Agent, or Firm*—Leydig, Voit & Mayer

[57] ABSTRACT

A whole blood control sample and a method of preparing the sample are disclosed. The method comprises collecting a whole blood sample from one or more donor, separating each sample into red blood cells and plasma, fixing the red blood cells, mixing the fixed red blood cells with plasma from the same or a different donor to produce a suspension, quick-freezing the suspension before the red blood cells can settle, and lyophilizing the frozen suspension. The control sample therefore comprises a lyophilized mixture of fixed red blood cells and plasma solids.

22 Claims, No Drawings

WHOLE BLOOD CONTROL SAMPLE

BACKGROUND OF THE INVENTION

1. Field of the Invention

This invention is related to the preparation and use of control samples designed to simulate blood having defined properties in clinical laboratory situations.

2. Background of the Invention

The field of clinical diagnosis has been rapidly expanding in recent years. Numerous new diagnostic techniques have been developed, and old techniques have been improved. Apparatus capable of making clinical measurements have also been an object of much development.

All of these laboratory methods and apparatus require periodic verification of their ability to perform properly. Verification is usually obtained using a control sample having a pre-determined property, typically a set value for the analyte concentration or other property being measured.

Control samples must have a number of properties in order to be effective. These include stability during storage times preferrably lasting several months or years, reproducibility, and ease of handling. When an analyte concentration is being measured, the control sample can typically be an aqueous solution of the analyte (if the analyte is stable in a aqueous solution) or a measured quantity of the analyte in the dry state to which water or another liquid is added. The manufacture of such control samples is relatively straightforward compared to complex biochemical control samples that are related to physical or biochemical properties of a complex substance such as whole blood.

A typical complex biochemical measurement requiring a complex control sample is prothrombin time coagulation testing, which requires the presence of complex plasma factors from the clotting cascade. Because of the difficulty in separating, purifying, and re-constituting such a complex sample, plasma is normally used as a control sample. This is satisfactory for the typical prothrombin time testing conducted in clinical laboratories, which is performed on an anti-coagulated plasma sample after reaction with calcium ion and a reagent. In the typical test, whole blood samples are collected by venipuncture into a citrate anti-coagulant. The citrate chelates the calcium ion, which is an essential factor in blood coagulation. The reagent added during the analysis contains excess calcium which neutralizes the excess citrate and restores the required level of calcium ion, allowing normal coagulation to occur so that a prothrombin time measurement can be made. Under these circumstances, a lyophilized citrated plasma control is sufficient for use as the control sample since the test does not depend on a physiological level of free calcium ion or the presence of the red blood cells in the sample.

However, lyophilized citrated plasma control samples are not sufficient for all types of available prothrombin time testing apparatus. U.S. patent application Ser. No. 762,748, filed Aug. 5, 1985, which is herein incorporated by reference, describes a simple device and method which requires the presence of red blood cells in a sample in order to determine prothrombin time. The device includes a capillary segment which acts as a pump, a reaction chamber at one end of the capillary, an inlet port for blood into the reaction chamber, and a vent at the other end of the capillary. The capillary and the reaction chamber provide for capillary flow due to surface tension and mixing of the assay medium with the reagent that is held in the reaction chamber. The reagent accelerates the coagulation process, which stops the flow of blood through the capillary. Blood flow is measured by the detection of the flow of red blood cells between a light source and a detector. Thus, any control sample must contain red blood cells or similar particles since it is the cessation of the motion of the particles that is detected by the instrument. Prior art plasma control samples are thus insufficient.

Fresh whole blood cannot be used as a control sample in such a device since clotting factors either deteriorate or are activated with the passage of time. Whole blood is therefore not sufficiently stable to allow its use as a control sample.

Accordingly, there is a need for a whole blood control sample for use in the apparatus described above and for use in other assays in which whole blood control samples would be advantageous.

BRIEF DESCRIPTION OF RELEVANT LITERATURE

Bing, et al., *Proc. Soc. Experimental Bio. Med.* (1967) 124:1165, describes procedures for the manufacture of aldehyde-fixed erythrocytes used in a hemagglutination assay of antigens and antibodies. Loelinger, et al., *Thrombo. Diath. Haemorrh (Stuttgard)* (1975) 33:172–190, describes a thromboplastin calibration procedure for the standardization of anticoagulation controls and preparation of lyophilized plasma standards. Maile, *Scand. J. Haemost.* (1980) 25:21–33, describes the use of reference plasmas in the control of oral anticoagulation therapy. van den Besselar, et al., *Thromb. Haemostasis* (1980) 43:53–57, describes calibration of thromboplastin measurements. Perkash, *Amer. J. of Clin. Path.* (May 1980) pp 676–681, describes the quantitative action of protamine and heparin on blood coagulation. A general discussion of blood clotting process is described in WHO Expert Committee on Biological Standardization: 33rd Report, WHO Technical Report Series 687:81–105 (1983).

SUMMARY OF THE INVENTION

A whole blood control sample is provided along with a method of producing the control sample. The control sample comprises a lyophilized mixture comprising fixed red blood cells and heparinized plasma solids. The plasma solids are obtained from a plasma sample containing a low concentration of heparin relative to the amounts typically used in preventing coagulation of blood with heparin. The plasma and red blood cells can be obtained from the same or different sources. Certain steps in the production of the control sample result in particularly advantageous samples. These steps include adjusting the mixture prior to lyophilization to a hematocryte of 35-45%, quick-freezing the sample prior to lyophilization, and adjusting coagulation time by manipulation of the sample. Typical manipulations of the sample include heating to partially destroy some of the clotting factors, thereby decreasing clotting speed, or co-mixing with a mammalian plasma to speed up clotting.

DESCRIPTION OF THE PREFERRED EMBODIMENTS

The present invention provides a whole blood sample which comprises a lyophilized mixture of fixed red blood cells and plasma solids. The control sample may also contain an anti-coagulant, typically heparin, and may contain a different mammalian plasma, which is present to increase the rate of coagulation.

The control sample can be prepared from either human or non-human mammalian blood. Typically, the same blood is selected for use in preparing the control sample that is used in the measuring technique for which a control sample is being prepared. For example, human blood is typically selected for use in preparing human control samples. However, the control sample does not need to be restricted to the same source as the test sample in most cases. For example, a sample designed for use in an apparatus which measures clotting would not normally depend on the type of blood cells being used unless the size of the red blood cells present was of particular importance (for example in traversing a small capillary tube). Nonetheless, in preferred embodiments of the invention human blood is used.

Both the red blood cells and plasma used to prepare the fixed red blood cells and the plasma solids are obtained by drawing whole blood from a blood donor. An anti-coagulant, typically heparin, is added in most cases to prevent coagulation during the remaining steps of production of the whole blood control sample and during its storage. Heparin is typically present at a concentration of from 0.5 to 5 units heparin/ml, preferrably from 1 to 2 units/ml. When used with the diagnostic technique described in U.S. patent application Ser. No. 762,748, filed Aug. 5, 1985, the presence of anti-coagulants other than those typically present in unmodified human whole blood is undesirable. Specifically, the typical anti-coagulation reagents EDTA, oxalate, and citrate should not be present. It should be recognized that a small amount of citrate is present in normal blood and the prohibition against calcium chelating agents other than those present in unmodified human whole blood refers to a prohibition of citrate being present in an amount greater than that considered to be normal. Normal amounts of citrate and any other components of whole blood mentioned in this specification are readily known to those skilled in the art to which this invention pertains and can be verified in the following references: Natelson et al., *J. Biol. Chem.* (1947) 170:597; Hodgkinson, A., *Clin. Sci.* (1963) 24:169.

However, when the control sample is being prepared for other uses or used in other methods of measuring clotting times, other anti-coagulants, such as citrate and EDTA, can be used.

After whole blood is collected from a donor, the red blood cells are separated from the plasma. Separation is typically carried out by centrifugation filtration, and/or washing. Separation is considered sufficient when the amount of plasma present in the red blood cells is no more than 0.10 percent by weight of the red blood cells, preferrably no more than 0.07%. Similarly, for the plasma portion, no more than 0.05 percent by weight of red blood cells should be present in the plasma, preferably no more than 0.02%.

The separated red blood cells are fixed with any of the normal fixing agents that are capable of preventing lysis of red blood cells upon freezing. Typically, a fixing agent will be chosen that cross-links proteins or other substances present on the surface membrane of the red blood cells. Typical cross-linking agents include aliphatic dialdehydes, which typically contain from 4–10 carbon atoms. Glutaraldehyde is a preferred dialdehyde.

Standard techniques of fixing with aliphatic dialdehydes can be carried out. This would typically consist of adding one volume of red blood cells to 2–4 volumes of an isotonic solution containing from 0.25 to 0.75 percent of the dialdehyde. Contact would be maintained for from 10 to 90 minutes, with the cells being stirred to prevent cross-linking between individual cells. The fixing solution is then removed from contact with the fixed red blood cells. The fixed red blood cells are typically stored in the cold until further use, typically at 2°–6° C.

The plasma portion of a whole blood sample is typically frozen immediately after the red blood cells are separated. Freezing prevents deterioration of any of the coagulation factors. However, if the plasma sample can be handled sufficiently quickly, freezing is not necessary. For example, if fixed red blood cells are available from another donor, they may be mixed with the plasma without freezing, and the remaining steps can be conducted using this mixture. Since the red blood cells used are fixed, thereby destroying the determinants responsible for interactions between different blood types, red blood cells and plasma can be used from different individuals, including individuals having different blood types. By blood types is meant both the typical A, B, AB, and O types caused by differences in the major histocompatability factors as well as other blood-type differences, such as Rh differences and differences caused by other histocompatability factors.

The plasma sample can be modified before the red blood cells are added to produce the whole blood control sample. Typical modifications are pooling of plasmas from different donors in order to provide a large number of control samples having the same biochemical characteristics, heating or otherwise treating in order to destroy at least a portion of the coagulation factors (thereby reducing the rate of coagulation), and adding plasma from a different mammalian species. Typical treatments used to destroy coagulation factors include solid-phase adsorption of factors with barium sulfate, aluminum hydroxide, asbestos, and/or antibodies.

Heat treatment to increase coagulation time is well known and is described in laboratory methods in Blood Coagulation by J. W. Eichelberger, Jr., Harper and Row, 1965. Additional references include Hematology Principals and Procedures, Brown, B. A., Lea and Fehiger, 1973, p. 120; and Technical Hematology, Simmons, A., Lippincott, 1968, pp. 171–204.

If plasma from another mammalian species is to be added, typical plasmas used when human blood is the source of the principal plasma include canine, rabbit, and bovine blood. When canine plasma is used, from 5 to 15 percent by volume is typically added. For example, in order to reduce the coagulation time by 25%, 10% of canine plasma is added to human blood.

The plasma, either treated or untreated, is mixed with fixed red blood cells to form a suspension. The suspension is generally stirred gently to prevent settling. In order to prevent the deterioration of the blood coagulation system in the plasma, the remaining steps are carried out as quickly as possible. The plasma is typically used either immediately after thawing (for frozen plasma) or immediately after the red blood cells have been separated (for fresh plasma). Blood without anticoagulant will coagulate in approximately 10 minutes. If the plasma sample contains heparin, as described above, coagulation will not take place.

Plasma and fixed red blood cells are blended to a final hematocrit of approximately 30-55%, preferably 35-45%. Typically the mixture will contain only plasma, optionally modified as described herein, and fixed red blood cells. However, it is possible to include other components such as stabilizers, antibiotics, and the like typically used with lyophilized biological samples.

Samples are withdrawn from the uniformly blended suspension and quick-frozen. The quick-freezing should be accomplished before the fixed red blood cells in the sample have had time to settle significantly. Typically, the sample should be frozen completely within 60 seconds after being withdrawn from the stirred suspension. A convenient means of accomplishing the quick-freezing is to apply a small sample of the suspension to a surface maintained at a temperature well below the freezing point of the suspension. Desirably, the surface is a surface of the container in which the sample will be maintained as a control sample. Typically, the surface will be maintained at a temperature at least 30° C., preferably at least 50° C., below the freezing point of the suspension. This can readily be accomplished by adding samples of the suspension to sample containers maintained in contact with dry ice, a solution containing dry ice, or a thermally conductive material in contact with dry ice.

After quick-freezing, the samples are lyophilized by removing water under vacuum. In order to maintain maximum stability of the control samples, they are typically isolated from the atmosphere by sealing the containers under vacuum.

The lyophilized control samples will contain fixed red blood cells and plasma solids. Heparin will comprise from 0.002 to 0.003 percent by weight of the dry product.

The lyophilized control samples can be reconstituted with water or other diluents by simply adding a measured quantity of water to the control sample and mixing gently. Samples prepared in the manner described above dissolve readily. When used as a prothrombin time control sample, the control samples are normally used within one hour of reconstitution.

The control samples are specifically designed for the prothrombin time measuring apparatus described in U.S. application Ser. No. 762,748, cited above. The apparatus of this system determines prothrombin time of blood obtained by a finger stick, or it can be used with any other small blood sample. The blood is introduced into the device through an inlet port which will introduce the sample into a chamber or a capillary. The sample will then transit the device passing through one or more capillaries or chambers where the sample will encounter one or more reagents, which reagents are involved in a system which produces a detectable signal. By having orifices which connect the pathway to the atmosphere at one or more sites, one can terminate the flow upon the fluid sample reaching that site so that the medium may be incubated for various times or movement stopped subject to the initiating movement, for example, immediately prior to measurement. Prothrombin time measurement is typically made by a light detector that detects the presence of a speckle pattern caused by light from a laser or other light source passing through some portion of the flow path. When flow ceases because of coagulation, the cessation of motion is measured as the end-point of the reaction. Details on the operation of the device can be found in the indicated patent application. When prothrombin time is being measured and heparin is included within the control sample (or the sample of blood being measured) a material antagonistic to the activity of heparin will be included in at least one reaction chamber or portion of the device in order to counteract the anti-coagulant nature of heparin. Two materials that typically can be used are polybrene and protamine-sulfate, both of which are known to neutralize the activity of heparin. Polybrene is 1,5-dimethyl-1,5-diazaundecamethylene polymethobromide.

In addition to use in the particular system described above, control samples can be used either specifically as describe herein or as modified to contain other analytes for use in other devices in which use of a whole blood control sample is desirable. For example, nearly any analysis that begins with whole blood would be aided by having a whole blood control sample as described in this application. If the test is for a particular analyte, that analyte can be added to the plasma while it is separated from the red blood cells. Then any variation between the actual sample and the control sample that is caused by the presence of red blood cells, for example during a separation technique, would be eliminated. For example, the whole blood control samples of the invention could be used in whole blood chemistry analyzers.

The invention now being generally described, the same will be better understood by reference to the following specific examples which are included for purposes of illustration only and are not to be considered limiting of the invention unless so specified.

EXAMPLES

WHOLE-BLOOD-CONTROL PREPARATION

A lyophilized whole blood control with stabilized, fixed human erythrocytes and plasma with a normal physiological calcium ion concentration was prepared. First, fresh whole blood (from a normal donor) was drawn into a cold heparin-saline solution. The heparin-saline anti-coagulant had an osmolality between 270–290 mos. Approximately 30 parts of whole blood are mixed with 1 part of the anti-coagulant solution. The final heparin concentration was between 1 and 2 usp units of heparin per ml blood.

The whole blood was centrifuged at 2°–8° C. to separate the plasma fraction from the red blood cells. Plasma units are pooled as needed.

The cell-free plasma was buffered with the addition of N-2-hydroxyethylpiperazine-N-2-ethanesulfonic acid at a molarity of 20 to 50 mM and adjusted to a physiologic pH.

Plasma to be used for a normal Prothrombin-Time control was modified by addition of nonhuman mammalian plasma to shorten the Prothrombin Time. Dog (canine), rabbit, or bovine plasma have been shown effective. A volume 5–15% of the human plasma was added. The adjusted plasma was frozen.

Plasma to be used for the abnormal or prolonged Prothrombin-Time control was heated slowly to 48° C. for 1–6 hours. When an aliquot of the heated plasma gave the desired Prothrombin Time, the plasma was removed from the heat and frozen.

The erythrocytes were washed two to three times with saline, to eliminate residual plasma, white cells and platelets. Units of washed red blood cells were pooled as needed. The pooled, washed erythrocytes were centrifuged, and the supernatent was removed. The packed erythrocytes were then added to two to four volumes of 0.25 to 0.75% gluteraldehyde while mixing well. After a period of 20 to 90 minutes, the fixed cells were centrifuged, washed in saline, and resuspended in a preservative solution. The preservative solution contained saline and antimicrobials. The fixed-cell suspension was stored at 2°–8° C. for a period of up to 3 months.

The final control preparation occured with the blending of thawed plasma with the washed fixed red blood cells. The plasma was thawed in a heated water bath. The red cell preservation solution was removed from the cells after centrifugation. Plasma was blended with the packed cells to hematocrit of 35–45%. The blend was carefully stirred to insure homogeneity.

This control material was dispensed into glass serum vials. The vials were precoated with an alkylsilane solution to minimize biochemical and/or physiological interactions of the blood control with the glass material. The glass vials into which the control is dispensed were in direct contact with a rapid-heat-conducting material at a low temperature ($-40°$ C. to $-100°$ C.). The control material is frozen as it makes contact with the cold vial. This fast freezing step is critical to insuring homogeneous lyophilization of the control materials. The heavier cells do not settle away from the plasma.

Once the material has been dispensed and frozen, it was lyophilized in a manner consistent with standard lyophilization procedures.

CONTROL USE

To reconstitute the whole blood controls, one removes the rubber stopper from the vial and adds water. The reconstitution volume is 250 $\mu$l for a vial filled to 275 $\mu$l. After the water is added, the vial is gently swirled until the lyophilized pellet has dissolved. An aliquot of blood is removed from the vial with any variety of disposable plastic pipetting device, and dropped onto the Biotrack Protime Cartridge sample site. The Prothrombin Time reagent present in the cartridge contains 0.001% polybrene to neutralize the heparin. The use of Biotrack Protime Cartridges (except for added polybrene) is described in a 1986 Biotrack publication entitled "Coumadin ® Control at Your Fingertips: Biotrack ® Protime Test System." The control is drawn into the reagent chamber where it reacts with the Prothrombin Time reagent and heparin neutralizing agent, and coagulation is initiated. The control-reagent reaction mixture continues to flow through the Biotrack Cartridge until coagulation is complete. With the formation of the endpoint clot, blood motion ceases.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A whole blood control sample, which comprises: a lyophilized mixture comprising (1) fixed red blood cells, and (2) plasma solids including coagulation factors capable of producing clotting, wherein said mixture prior to lyophilization comprises 30–55% fixed red blood cells and 70–45% plasma.

2. The control sample of claim 1, wherein said sample contains herapin or a calcium chelating agent selected solely from chelating agents present in unmodified human whole blood.

3. The control sample of claim 2, wherein said sample contains no added citrate.

4. The control sample of claim 1, wherein said red blood cells are fixed with an aliphatic dialdehyde.

5. The control sample of claim 4, wherein said dialdehyde contains from 4 to 10 carbon atoms.

6. The control sample of claim 5, wherein said dialdehyde is glutaraldehyde.

7. The control sample of claim 1, wherein heparin is present in from 0.002 to 0.003 percent by weight of said lyophilized mixture.

8. The control sample of claim 1, wherein said fixed red blood cells and said plasma solids are obtained from two different human donors.

9. The control sample of claim 8, wherein said individuals have different blood types.

10. The control sample of claim 1, wherein said mixture further comprises plasma solids from a mammalian host different from the host that supplied the principal plasma solids.

11. The control sample of claim 10, wherein said plasma solids are human and canine plasma solids.

12. A method of preparing a whole blood control sample, which comprises:
collecting a whole blood sample from one or more donors;
separating each whole blood sample into red blood cells and plasma;
fixing said red blood cells;
mixing said fixed red blood cells with plasma from the same or a different donor to produce a suspension containing 30–55% fixed red blood cells and 70–45% plasma including coagulation factors capable of producing clotting;
quick-freezing said suspension before said red blood cells can settle; and
lyophilizing said frozen suspension.

13. The method of claim 12 wherein said plasma sample is mixed with plasma from a different mammal prior to said mixing with fixed red blood cells.

14. The method of claim 13, wherein said different mammal is a dog and said one or ore donors are human.

15. The method of claim 12, wherein heparin is added to said whole blood sample prior to said separating.

16. The method of claim 15, wherein the heparin concentration of said whole blood sample is from 0.5 to 3 USP units/ml.

17. The method of claim 12, wherein said red blood cells are fixed with an aliphatic dialdehyde.

18. The method of claim 17, wherein said dialdehyde is glutaraldehyde.

19. The method of claim 12, wherein said quickfreezing is accomplished in less than 60 seconds.

20. The method of claim 19, wherein said quick-freezing is accomplished by applying a small sample of said suspension to a surface maintained at a temperature below the freezing point of said suspension.

21. The method of claim 20, wherein said temperature is no more than $-20°$ C.

22. The method of claim 12, wherein said control sample is stored under vacuum after said lyophilizing.

* * * * *